US007335401B2

(12) United States Patent
Finke et al.

(10) Patent No.: US 7,335,401 B2
(45) Date of Patent: Feb. 26, 2008

(54) METHOD FOR PRODUCING MICROPARTICLES LOADED WITH PROTEINS

(75) Inventors: Andreas Finke, Penzberg (DE); Ursula Klause, Peissenberg (DE); Federic Donie, Penzberg (DE); Rupert Herrmann, Weilheim (DE); Herbert Von Der Eltz, Weilheim (DE); Peter Sluka, Weilheim (DE); Wolfgang Jona, Waldkraiburg (DE)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 0 days.

(21) Appl. No.: 10/774,325

(22) Filed: Jul. 12, 2004

(65) Prior Publication Data
US 2005/0079545 A1    Apr. 14, 2005

Related U.S. Application Data

(63) Continuation of application No. PCT/EP02/08789, filed on Aug. 7, 2002.

(30) Foreign Application Priority Data
Aug. 10, 2001    (EP)    ................... 01118812

(51) Int. Cl.
B05D 7/00    (2006.01)
G01N 33/553    (2006.01)
G01N 33/546    (2006.01)

(52) U.S. Cl. .................. 427/414; 436/526; 436/533

(58) Field of Classification Search ................ 427/414, 427/214, 220, 222, 338; 428/407, 403; 424/78.08, 424/460, 491; 436/533–534, 86; 435/7.1, 435/7.5, 7.8, 177, 180–181, 814; 106/38.4; 530/350, 402, 421, 810, 812, 815–816
See application file for complete search history.

(56) References Cited

U.S. PATENT DOCUMENTS

| 4,228,237 | A | * | 10/1980 | Hevey et al. | .................. | 435/5 |
| 4,329,151 | A | * | 5/1982 | Lou et al. | .................. | 436/533 |
| 4,478,914 | A | | 10/1984 | Giese | .................. | 428/407 |
| 4,656,252 | A | | 4/1987 | Giese | .................. | 530/350 |
| 5,061,640 | A | * | 10/1991 | Tischer et al. | .................. | 436/527 |
| 5,175,112 | A | * | 12/1992 | Amiral et al. | .................. | 436/533 |
| 5,512,439 | A | * | 4/1996 | Hornes et al. | .................. | 435/6 |
| 5,686,244 | A | * | 11/1997 | Gudibande et al. | .................. | 435/6 |
| 5,858,648 | A | * | 1/1999 | Steel et al. | .................. | 435/5 |
| 6,462,809 | B1 | * | 10/2002 | Ryan et al. | .................. | 356/128 |
| 6,638,728 | B1 | * | 10/2003 | Desai et al. | .................. | 435/7.5 |

FOREIGN PATENT DOCUMENTS

DE    199 24 643 A1    11/2000

WO    WO 96/03652    2/1996

OTHER PUBLICATIONS

Vaynberg, K.A., Wagner, N.J., and Sharma, R. (2000) "Polyampholyte Gelatin Adsorption to Colloidal Latex: pH and Electrolyte Effects on Acrylic and Polystyrene Latices," Biomacromolecules 1, 466-472.*
Bocquier AA, Potts JR, Pickford AR, Campbell ID (1999) "Solution Structure of a Pair of Modules from the Gelatin-Binding Domain of Fibronectin," Structure 7:1451-1460.*
Jolley ME, Wang CH, Ekenberg SJ, Zuelke MS, Kelso DM (1984) "Particle concentration fluorescence immunoassay (PCFIA): a new, rapid immunoassay technique with high sensitivity," J Immunol Methods 67:21-35.*
Ortega Vinuesa, J. L.; Galvez Ruiz, M. J.; Hidalgo-Alvarez, R. (1996) Langmuir 12:3211-3220.*
Bangs, L.B. (1996) "New developments in particle-based immunoassays: introduction," Pure & Appl. Chem. 10:1873-1879.*
Bohidar, H.B. "Hydrodynamic properties of gelatin in dilute solutions" (1998) International Journal of Biological Macromolecules 23:1-6.*
Van Oss et al. "The binding of immune globulins and other proteins by polystyrene latex particles" (1966) J. Reticuloendothel Soc. 3:29-40.*
Suzawa et al. "Absorption of Plasma Proteins onto Polymer Latices" Advances in Colloid and Interface Science (1991) 35:139-172.*
Rossjohn et al. "Structure of a Cholesterol-Binding, Thiol-Activated Cytolysin and a Model of Its Membrane Form" Cell 89:685-692 (1997).*
Weis et al. "Streptolysin O: the C-terminal, tryptophan-rich domain carries functional sites for both membrane binding and self-interaction but not for stable oligomerization" Biochimica et Biophysica Acta 1510 (2001) 292-299.*
Spaeth et al. "Studies on the Biotin-Avidin Multilayer Adsorption by Spectroscopic Ellipsometry" Journal of Colloid and Interface Science 196, 128-135 (1997).*
Morgan et al. "Modeling the Bacterial Protein Toxin, Pneumolysin, in Its Monomeric and Oligomeric Form" Journal of Biological Chemistry 269 25315-25320 (1994).*
Serra, J. et al. "On the adsorption of IgG onto polystyrene particles: electrophoretic mobility and critical coagulation concentration" Colloid Polym Sci 270:574-583 (1992).*
Kadima et al. Biophys. J. vol. 57 (1990), p. 125-132.*
Vaynberg et al. Journal of Colloid and Interface Science 205 (1998), 131-140.*
Kakabakos et al. "Immobilization of Immunoglobulins onto Surface-Treated and Untreated Polystyrene Beads for Radioimmunoassays" Clin. Chem. 36 (1990), 492-496.*
Song et al. "Effects of Cosolvents and pH on Protein Adsorption on Polystyrene Latex: A Dynamic Light Scattering Study" Journal of Colloid and Interface Science 221 (2000), 25-37.*

(Continued)

*Primary Examiner*—Long V. Le
*Assistant Examiner*—Christine Foster
(74) *Attorney, Agent, or Firm*—Barnes & Thornburg LLP

(57) ABSTRACT

The present invention concerns a method for producing microparticles loaded with proteins which is characterized in that the microparticles are loaded in suspension under strongly alkaline conditions. The invention also concerns microparticles which can be produced using this method and their use in a binding test e.g. in an immunoassay.

8 Claims, 4 Drawing Sheets

OTHER PUBLICATIONS

Will et al. "Dynamic Viscosity Measurements by Photon Correlation Spectroscopy" International Journal of Thermophysics, vol. 16 (1995), pp. 433-434.*

Schmidt, H.H.J., Genschel, J.C., Wagner, S., Manns, M.P. "Quantification of lipoprotein(a): Comparison of an Automated Latex-Enhanced Nephelometric Assay with an Immunoenzymometric Method", Eur J. Clin Chem Clin Biochem, 1996; 34: 119-124.

Cantarero, L.A., Butler, J.E., Osborne, J.W., "The Adsorptive Characteristics of Proteins for Polystyrene and Their Significance in Solid-Phase Immunoassays", Analytical Biochemistry 105, 375-382 (1980).

Illum, L., Jones, P.D.E., "Attachment of Monoclonal Antibodies to Microspheres", Methods in Enzymology, vol. 112, 1985, pp. 68-84.

Ishikawa, E., Hamaguchi, Y., Imagawa, M., "An Improved Preparation of Antibody-Coated Polystyrene Beads for Sandwich Enzyme Immunoasay", Journal of Immunoassay, 1(3), 385-398 (1980).

Conradie, J.D., Govender, M., Visser, L., "ELISA Solid Phase: Partial Denaturation of Coating Antibody Yields a More Efficient Solid Phase", Journal of Immunological Methods, 59 (1983) 289-299.

Hermanson, G. T., Bioconjugate Techniques, "Hobobifunctional Cross-Linkers," Academic Press, 1996, p. 187-237.

* cited by examiner

METHOD FOR PRODUCING MICROPARTICLES LOADED WITH PROTEINS

RELATED APPLICATIONS

This application is a continuation of international application PCT/EP02/08789 filed Aug. 7, 2002 and claims priority to European application EP 01118812.5 filed Aug. 10, 2001.

FIELD OF THE INVENTION

The present invention concerns a method for producing microparticles loaded with proteins which is characterized in that the microparticles are loaded in suspension under strongly alkaline conditions. The invention also concerns microparticles which can be produced by this method and their use in a binding test, e.g., in an immunoassay.

BACKGROUND OF THE INVENTION

Microparticles loaded with proteins are known and are often used as a solid phase in medical, immunological, and diagnostic test procedures. The unloaded initial particles (also referred to as beads) are mainly composed of latex, e.g., polystyrene latex, and can often be magnetized due to a content of magnetite or a core made of magnetite. Proteins are usually coupled to the latex particles in a well-known manner by means of chemical linkers (covalent binding) or by adsorption (non-covalent binding).

The covalent coupling methods described in the prior art use microparticles (functionalized particles) as a starting material which have various functional groups (—COOH, -tosyl, -epoxy etc.). These functional groups are used to form covalent bonds with the proteins, e.g., via amino or carboxy groups on the proteins to be coated.

Covalent coupling methods differ from adsorptive coupling methods in that the functionalized particles used in the former case have a considerably more hydrophilic surface than non-functionalized particles. This reduces the amount of adsorptively bound protein. Adsorptively bound proteins can cause bleeding depending on the binding strength. "Bleeding" means that protein that is unbound or only weakly bound becomes detached. Only protein that has covalently reacted with the functional groups on the particle surface is permanently bound.

However, the initial particles used for covalent coating methods exhibit a high degree of lot to lot variability with regard to the density of functional groups, and the functional groups on the surface have a low storage stability which results in low loading densities and/or very variable results after loading. Another disadvantage of covalent coating methods is that the spatial accessibility of the functional groups is often poor. For this reason the loading densities required for an application, e.g., in a sensitive immunoassay, are often not achieved with particles coated in this manner. Covalent chemical coupling can also result in an inactivation of the coated protein.

Giese discloses coupling methods in U.S. Pat. No. 4,478,914 and U.S. Pat. No. 4,656,252 which enable a multilayer loading of surfaces with functional protein. In these methods biotin was covalently bound to the surface, subsequently avidin and a biotin-coupled extender was repeatedly bound to the loaded material, and unbound substance was removed by washing. In such a multilayer method a delayed bleeding can occur due to delayed desorption.

Particles with a hydrophobic surface are usually used for adsorptive coating methods. Known examples of such particles are polystyrene particles that are free from the functional groups discussed above or polystyrene particles that are derivatized with polyurethane.

Experience shows that particles that have been manufactured by adsorptive coating tend to have a higher bleeding tendency than covalently coated particles. This increased bleeding is due to the fact that the adsorptive coating occurs by means of relatively weak ionic and van der Waals interactions.

A number of tricks are known from the prior art for improving the adsorptive binding of proteins to surfaces and reducing the bleeding tendency. DE 19924643 describes the coating of particles at elevated temperatures and subsequent irradiation by UV light. These measures reduce the bleeding tendency.

Conradie, J. D. et al., J. Immunol Methods 59 (1983) 289-99 report a more efficient coating of microtitre plates by using elevated temperatures, high salt concentrations, or under acidic pH conditions.

Ishikawa, E. et al., J. Immunoassay 1 (1980) 385-98 also describe the advantageous use of strongly acidic pH conditions. They also recommend pretreating antibodies at pH 2.5 for coating polystyrene beads.

An additional disadvantage of the methods known from the prior art is the strong tendency of the hydrophobic particles to aggregate. The basic hydrophobic structure of the particles results in an increased tendency of these particles to form aggregates with one another which has a disadvantageous effect on the measurement accuracy in subsequent methods of determination using these particles. Furthermore these particles also have an increased tendency to unspecifically bind sample components when used in immunological tests due to their hydrophobic properties. Unspecific binding in such test systems is well-known to have a negative effect on test characteristics such as the signal-to-noise-ratio, or it can lead to false-positive and also to false-negative results.

In conventional wash steps the loaded particles are sedimented by centrifugation or magnetic separation and subsequently resuspended. The centrifugation or sedimentation has the effect that the loaded particles come very close to one another and in an unfavorable case form aggregates.

SUMMARY OF THE INVENTION

Hence the object of the present invention was to provide a method which allows the manufacture of adsorptively loaded microparticles on an industrial scale. Furthermore the invention also intends to provide protein-loaded microparticles that can be obtained by loading under strongly alkaline conditions and have a high binding capacity while at the same time having a low degree of bleeding and a good storage stability. The invention also encompasses advantageous applications of the microparticles coated under alkaline conditions in immunological detection systems.

According to an embodiment of the invention this object is achieved by a method for producing microparticles loaded with protein which is characterized in that the loading is carried out under strongly alkaline pH conditions. The coating is preferably carried out at a pH which is selected between pH 10.0 and pH 12.5.

The pH dependency of the coating for DYNAL M-270 beads (Dynal Biotech ASA) is shown. There is a pronounced increase in the measured signal in the pH range of pH 9.0 to pH 12.5 when using beads loaded under various pH conditions under otherwise the same test conditions in a TSH test. The results of a TSH assay are given as counts on the Y-axis.

Figure 2:
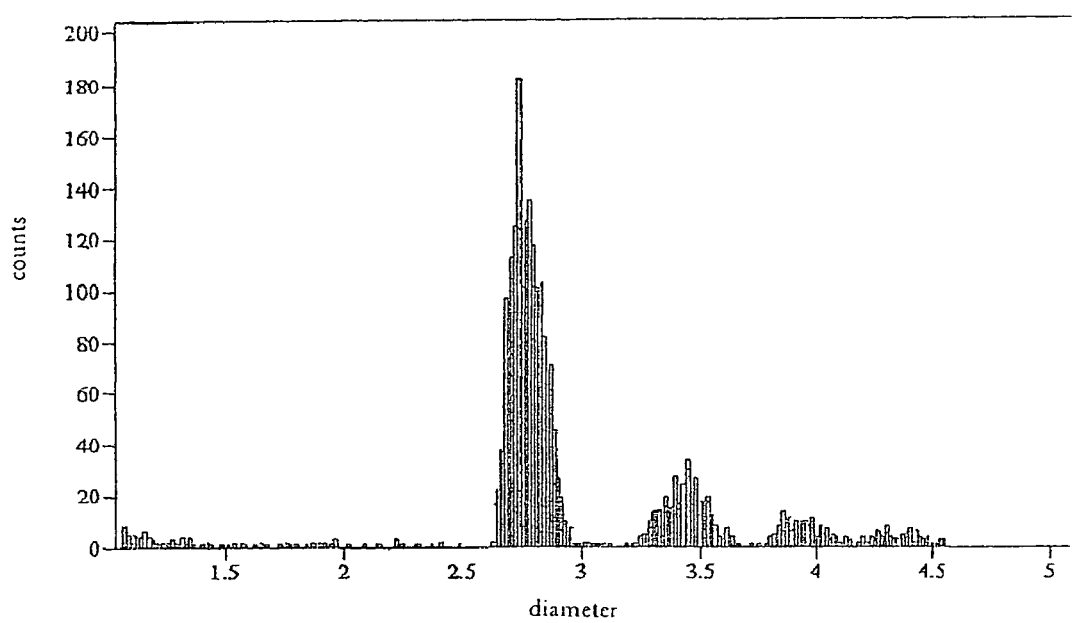

FIG. 2: Particle distribution when M-280 beads are coated by a standard method

DYNAL M-280 beads were coated as described in DE 19924643. The particle distribution was examined with a particle counting instrument (Coulter Multisizer II). The main peak at about 2.8 μm corresponds to monodisperse particles whereas the secondary peaks represent dimeric aggregates and aggregates of three or more particles.

Figure 3:
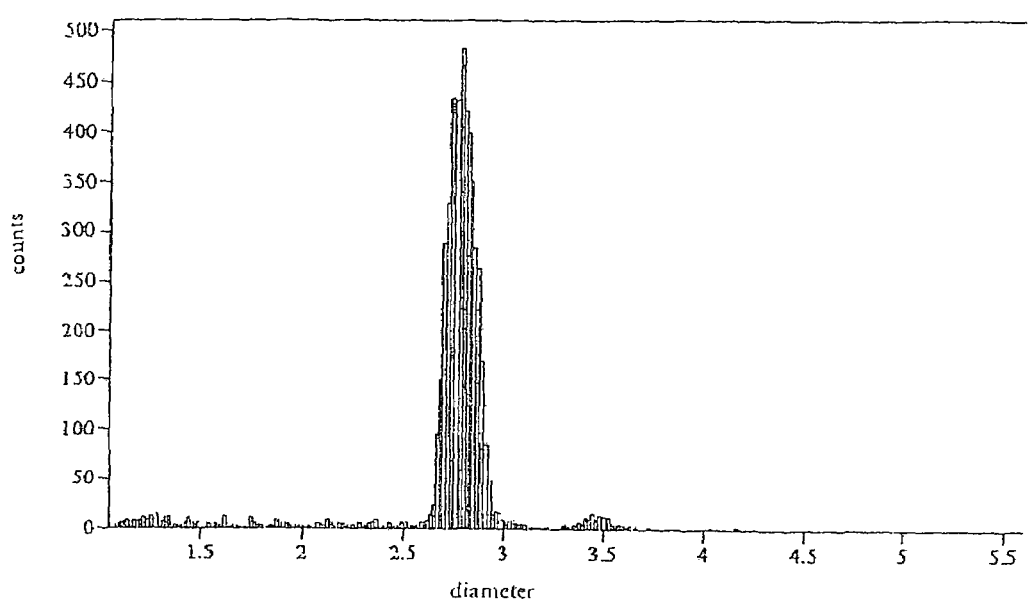

FIG. 3: Particle distribution when M-280 beads are coated in the method according to the invention DYNAL M-280 beads were coated as described in Example 1. The particle distribution was examined with a particle counting instrument (Coulter Multisizer II). The analysis showed that there was only a very small amount of dimeric aggregates. Larger aggregates are not evident.

Figure 4:
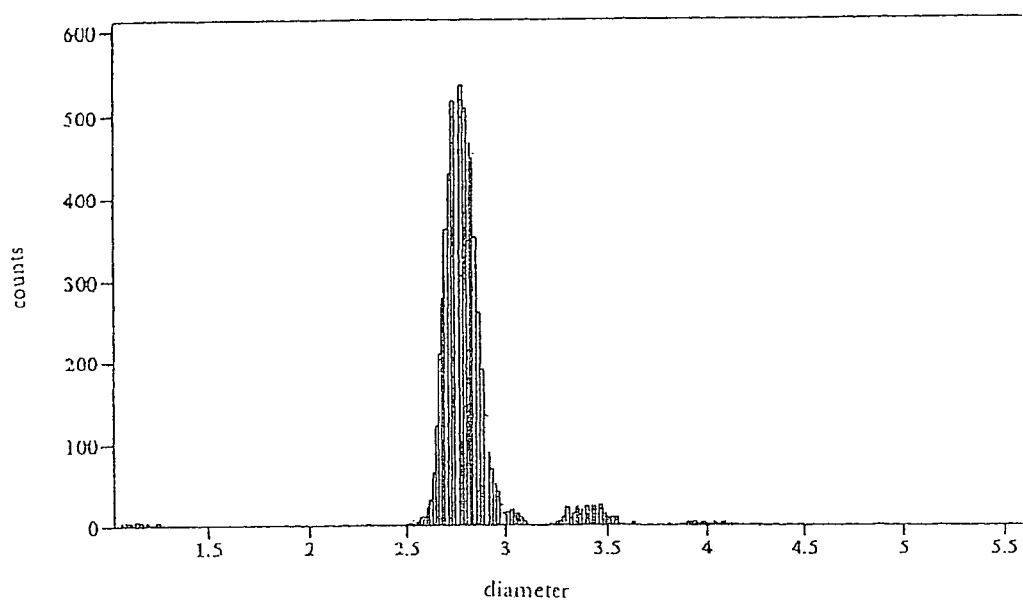

FIG. 4: Particle distribution when M-270 epoxy beads are coated in the method according to the invention DYNAL M-280 beads were coated as described in Example 1. The particle distribution was examined with a particle counting instrument (Coulter Multisizer II). The analysis shows that there is only a very small amount of dimeric aggregates. Larger aggregates are not evident.

DETAILED DESCRIPTION OF THE INVENTION

The microparticles (or beads) that are to be loaded and which can be used for the method of the present invention are microdispersed and are used in suspensions at concentrations of less than 20%, particularly preferably less than 10% weight per volume, a range of 0.1 to 10% weight/vol and in particular of 0.2 to 2% weight/vol being preferred.

In contrast to the prior art the present invention allows the advantageous use of hydrophobic particles as well as particles functionalized with epoxy groups in a process for adsorptive coating.

The particles can consist of latex and similar materials, preferably of polystyrene latex and may optionally contain magnetizable material such as magnetite. The particle size of the uncoated particles is preferably in a range of 50 nm to 25 μm. In the case of magnetic particles the preferred size is in a range of 0.5 μm to 25 μm since magnetic separation works particularly well in this range. DYNABEADS from the DYNAL Company having a size of ca 2.8 μm and consisting of 88% polystyrene and 12% magnetite such as the hydrophobic beads M-280 or the epoxy beads M-270 are, for example, suitable.

In a preferred embodiment the coating method according to the invention is additionally characterized in that the polystyrene particles have a hydrophobic surface or a surface functionalized with epoxide groups.

The use of polystyrene particles which have a magnetizable core is particularly preferred.

The protein material which is to be bound to the particles that is preferably polymerized has a size of at least 10 nm up to a maximum of 300 nm determined by photon correlation spectroscopy (PCS) (Lagaly, G., et al., photon correlation spectroscopy in "Dispersionen und Emulsionen" (1997) 289-294, Darmstadt, Steinkopf), a size range from 20 nm to 250 nm being preferred. In principle it is possible to use proteins having a molecular weight of more than 10 kD to load the microparticles. The protein to be coated is preferably a partner of a bioaffinity binding pair. Bioaffinity binding pairs are for example antigen/antibody, hapten/antibody and ligand/receptor.

One partner of such a binding pair which is preferably an antibody or receptor is used for the coating. A receptor for biotin such as avidin and in particular streptavidin is particularly preferred. Particularly suitable materials for the present invention are high molecular weight proteins or polymerized proteins such as polymerized streptavidin (SA-poly). It was found that polymerized proteins bind more strongly to surfaces in an adsorptive manner. The reason is probably because polymerized proteins have a higher number of contact sites. Hence these polymers would still be able to ensure an adequate binding to the surface even when individual contact sites become detached. In the case of monomers having a few to a single contact site the whole monomer is released as soon as the contact site becomes detached.

Polymerization of streptavidin can be achieved in a known manner by chemical treatment. Polymerized avidin or streptavidin and particularly preferably polymerized streptavidin is preferably used in a coating method according to the invention. Polymerized antibodies are also particularly suitable.

As mentioned above bleeding is a major problem especially during long-term storage and during particle transport. Bleeding is determined by separating the particles from the incorporated suspension and measuring the content of binding partner that has bled out in the supernatant.

For particles which have been coated with streptavidin the bleeding tendency is stated in nanogram streptavidin per milligram microparticles (ng/mg). This means that the binding capacity of the streptavidin that has bled away is determined by means of a calibration curve that has been determined using monomeric streptavidin. The bleeding of the SA beads produced according to the invention is preferably <150 ng/ml and particularly preferably <80 ng/ml.

As already mentioned a pivotal element of the present invention is the fact that the coating is carried out under strongly alkaline pH conditions. A pH range of pH 10.0 to pH 12.5 has proven to be particularly suitable. Depending on the duration of the coating procedure, different subranges of this pH spectrum may prove to be optimal. On an industrial scale the coating is preferably carried out for a period of 1-10 days. It is particularly preferable to carry out the coating for 4-7 days. When using these relatively long time intervals, pH ranges of 10.5 to 12.5 and in particular of 11.0 to 12.0 are particularly preferred. If shorter coating times are used, higher pH optima may result.

It has also proven to be advantageous to adjust the salt concentration of the alkaline buffer used for coating to a physiological salt range or higher. The coating is preferably carried out with a buffer which has a salt content of 0.1 to 2 M, particularly preferably 0.3 to 1.5 M and especially preferably of 0.8 to 1.2 M.

In a method according to the invention the microparticle suspension is preferably contacted with the high molecular weight protein material at 15-30° C. and particularly preferably at room temperature i.p. at ca 18-25°C., hence the protein material is not preheated. After loading under strongly alkaline buffer conditions, it is possible to already carry out a first or several separation step(s) which are used to remove weakly adsorbed or non-adsorbed protein.

The separation can be carried out by conventional methods such as magnetic separation in the case of microparticles containing magnetite. A separation in a microfiltration unit by sieves, filters or membranes is preferred for the method of the present invention. These may be hydrophilic or hydrophobic, however, in the latter case it is preferable to convert them into a hydrophilic state before use which can be achieved in a conventional manner. They preferably have a pore size which lies between the size of the microparticles and the size of the high molecular weight protein material. Particularly suitable pore sizes are in the range above about 50% of the size of the protein to be separated, i.e. ca. 50 nm to 2.5 µm. Membranes having pore sizes of 0.4 µm, preferably 0.45 µm to 2.5 µm, preferably up to 2 µm are particularly suitable.

The separation can be carried out once or several times in which a buffer or a buffer system consisting of different buffers can be used. The buffers preferably contain salts and detergents for displacing/solubilizing unbound proteins or proteins that have only been weakly bound, and so-called blocking agents (e.g. serum albumin) for filling up areas of the particle surface that may still be free. The separation step is preferably carried out several times, in particular three times using different buffers which differ from one another in their salt and detergent content. 5 to 15 times the batch volume is replaced during the separation. The effectiveness of the separation depends especially on the separation time (time during which the particles are suspended in a certain buffer solution) and the flow and pressure as well as combinations thereof in the separation system. The flow and pressure depend on the system that is used and can be determined by a person skilled in the art. Separated buffer can be determined by measuring the filling level and can be accordingly replaced by fresh buffer.

It is preferable to take care that the microparticles do not sediment during the entire procedure. It is particularly advantageous to also avoid sedimentation during the separation. For this purpose the suspension has to be agitated in a suitable manner which can for example be achieved by stirring, pump recirculation, introducing dispersing energy or any combination of such measures or by other suitable physical methods.

The loaded particles are also filled in an appropriate filling module preferably in a sterile manner.

The invention also concerns coated microparticles that can be obtained by the above-mentioned method.

The invention also concerns a method for detecting an analyte in a sample by contacting the sample with one or more analyte-specific binding partners, the method being characterized in that a microparticle coated according to the invention with a partner of a bioaffinity binding pair is used. The method is preferably carried out as an immunoassay. This means that at least one of the analyte-specific binding partners is an immunological binding partner. In this method the sample in which it is assumed the analyte is present is incubated with an immunologically specific binding partner. In the case of an antigen test such as for tumour markers like PSA, this immunologically specific binding partner is an antibody or a fragment thereof which binds specifically to the analyte, i.e., the tumour antigen PSA. In methods for detecting antibodies against a particular antigen, e.g. anti-HCV antibodies, the corresponding antigen can, for example, be used as the immunologically specific binding partner.

An immunological binding partner is preferably conjugated with the second partner of the bioaffinity protein used for the coating. If streptavidin has been used for the coating, the immunological binding partner is biotinylated. After carrying out the conventional incubation steps familiar to a person skilled in the art, the particles can be separated from the sample, and the amount of analyte found can be determined in a known manner.

Hence another subject matter of the invention is the use of microparticles coated according to the invention in an immunoassay.

In routine diagnostics the simplification of test procedures (as few as possible incubation steps with the lowest risk of errors) and provision of everything needed (all essential test components from one source, preferably in one package) is very far advanced. Usually a set of reagents (a kit) is delivered to the customer which contains all test-relevant components. Hence another subject matter of the invention is a test kit containing a suspension of microparticles that have been coated according to the invention.

The invention is further illustrated by the following examples, publications, and figures whose protective scope derives from the patent claims. The described methods are to be understood as examples which still describe the subject matter of the invention even after modifications.

SPECIFIC EMBODIMENTS

Example 1

Bead Coating 1.1 Reference Beads

DYNAL M-280 beads were coated as described in DE 19924643.

1.2 Alkaline Coating (pH Optimization)

Figure 1:
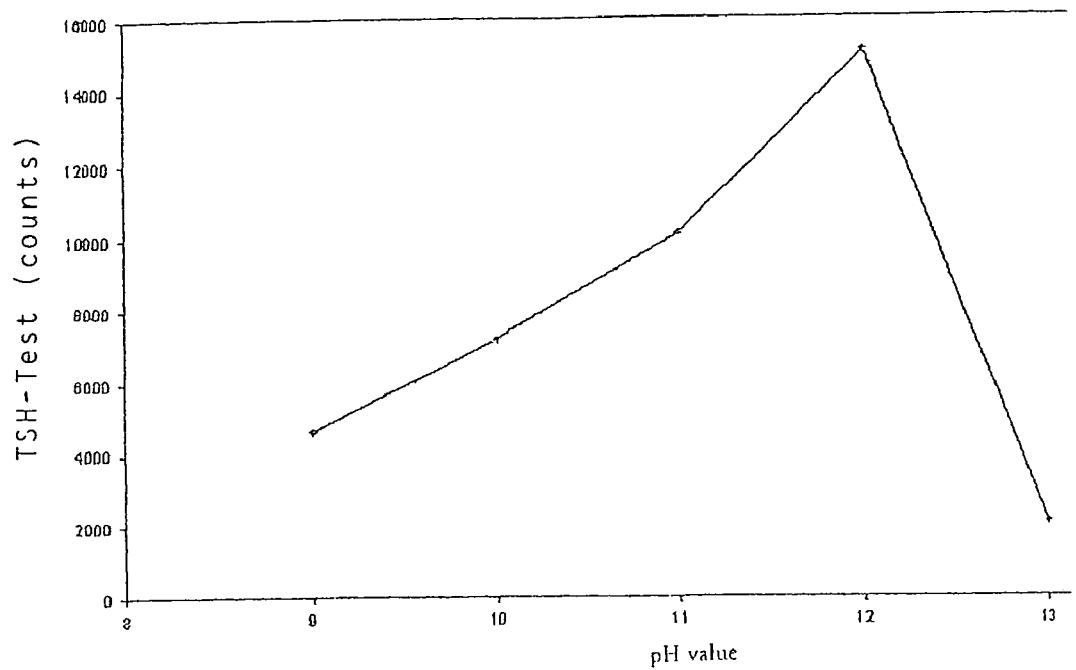
FIG. 1: pH dependency of the coating

50 mg magnetic beads (DYNAL M-270 or DYNAL M-280) were washed successively, first with isopropanol, then several times with 5 ml portions of 50 mM Na phosphate buffer (pH 9.0). Subsequently the beads were resuspended in 4 ml 50 mM Na phosphate buffer (pH 9.0). Afterwards 10 mg polymerized streptavidin (poly-SA) dissolved in 1 ml 50 mM Na phosphate buffer pH 6.3 was added. The pH was then adjusted to the desired value between pH 10.0 and pH 12.5 with NaOH. The preparation was incubated for 72 hours on a roller mixer. Subsequently the beads were washed alternately with 40 mM Na phosphate buffer (pH 7.4) and 1 percent TWEEN 20 (ICI Americas Inc.) solution (in the same basic buffer). The beads were subsequently incubated and washed several times with a solution consisting of sodium phosphate buffer (10 mM Na phosphate 0.15 M NaCl, pH 7.4) and BSA (0.5% w/v). Afterwards the beads were washed with 50 mM HEPES buffer (pH 7.4) and adjusted to a final concentration of 0.7 mg/ml in this HEPES buffer (pH 7.4). The suitability of the coated particles for use in an immunoassay was determined in a TSH test (thyroid stimulating hormone=TSH) and is shown graphically in FIG. 1 for the M-270 particles. It is evident that the selected alkaline conditions considerably improve the counts and thus the suitability of the particles in the test.

1.3 Alkaline Coating (Routine Method)

50 mg magnetic beads (DYNAL M-270 or DYNAL M-280) were washed successively firstly with isopropanol, then several times with 5 ml portions of 50 mM Na phosphate buffer (pH 9.0). Subsequently the beads were resuspended in 4 ml 50 mM Na phosphate buffer (pH 9.0).

Afterwards 10 mg polymerized streptavidin (poly-SA) dissolved in 1 ml 50 mM Na phosphate buffer pH 6.3 was added. The pH was then adjusted to the desired value between pH 10.0 and pH 12.5 with NaOH. The preparation was incubated for 4 to 7 days on a roller mixer. Subsequently the beads were washed alternately with 40 mM Na phosphate buffer (pH 7.4) and 1 percent TWEEN 20 solution. The beads were subsequently incubated and washed several times with a solution consisting of sodium phosphate buffer (10 mM Na phosphate 0.15 M NaCl, pH 7.4) and BSA (0.5% w/v). Afterwards the beads were washed with 50 mM HEPES buffer (pH 7.4) and adjusted to a final concentration of 0.7 mg/ml in this HEPES buffer.

EXAMPLE 2

Particle Distribution

The DYNAL M-280 and M-270 beads coated by the method described above were compared with M-280 beads coated by a conventional method using a particle counter (Coulter Multisizer II, FIGS. 2-4). In the case of the alkaline coating the result was a considerably more homogeneous distribution of the coated beads with substantially lower proportions of dimeric, trimeric, and higher aggregates. This is shown by comparing FIGS. 3 and 4 with FIG. 2.

EXAMPLE 3

Bleeding Properties

The bleeding of coated proteins occurs very slowly under normal storage conditions (4-8° C.) over many months. In order to simulate bleeding under storage conditions, a short-term model was used. For this the coated particles were stored for 21 days at 35° C. on a roller mixer. The biotin binding capacity of the supernatant which is due to streptavidin that has bled off is determined, for example, using radioactively labelled biotin.

The bleeding tendency is stated in ng as SA/mg particles. In order to determine the bleeding, a standard curve is established using monomeric streptavidin, and the biotin binding capacity of the supernatant of stressed microparticle suspensions is read off from this curve. In the case of the microparticles coated according to Example 1, the bleeding tendencies were surprisingly low and were regularly below 150 ng/mg, and in most cases even less than 100 ng/mg after stress.

EXAMPLE 4

Results in a HIV Function Test

A double antigen bridge test was carried out to detect specific antibodies against HIV. The sample liquid was incubated with a biotinylated antigen in the presence of a streptavidin-coated solid phase (magnetic SA beads prepared by a standard method or by one of the methods claimed here). After a washing step the same antigen was again added but in a ruthenium-labelled form. The presence of anti-HIV antibodies in the sample liquid was determined by means of the ruthenium label on the solid phase on the basis of electrochemiluminescence in an ELECSYS system (Roche Diagnostics GmbH).

A HIV peptide from the gp36 region of HIV 2 (a more detailed description is given in WO 96/03652) was used as an antigen that is labelled at the N-terminus. The concentration of the antigen in the test was 6 ng/ml biotinylated Ag, 200 ng/ml ruthenylated Ag.

The system blank value was determined in the absence of ruthenylated antigen.

The results of the experiments with the SA beads coated according to the invention which were based on DYNAL M-280 starting particles in comparison with particles that were coated according to the prior art are shown in the following tables.

TABLE 1

HIV test/measured values

| [counts] | streptavidin beads according to example 1 | streptavidin beads according to the prior art |
|---|---|---|
| system blank value | 316 | 481 |
| negative sample | 560 | 2,150 |
| positive sample 1 | 2,442,861 | 2,506,269 |
| positive sample 2 | 1,073,515 | 1,338,978 |
| positive sample 3 | 7,315 | 11,802 |

The signal dynamics were calculated according to the formula (signal−system blank value)/(negative sample−system blank value)

TABLE 2

HIV test/signal dynamics

| signal dynamics pos./neg. sera | streptavidin beads according to example 1 | streptavidin beads according to the prior art |
|---|---|---|
| negative sample | 1.0 | 1.0 |
| positive sample 1 | 10,010.4 | 1,501.4 |
| positive sample 2 | 4,398.4 | 802.0 |
| positive sample 3 | 28.7 | 6.8 |

It is apparent that considerably lower blank values are obtained by using the SA beads according to the invention, and this is associated with an improved differentiation of positive to negative signals.

The next table shows the unspecific binding of the antibody conjugate to the streptavidin solid phase. In this test procedure only buffer is used instead of the biotinylated antigens. The concentration of the ruthenium conjugate is 600 ng/ml.

TABLE 3

Unspecific binding of the Ru conjugate from the HIV test

| [counts] | streptavidin beads according to example 1 | streptavidin beads according to the prior art |
|---|---|---|
| system blank value | 316 | 481 |
| buffer | 446 | 2,061 |
| human serum | 373 | 692 |

Also in this case the beads according to the invention exhibit the better blank values (lower unspecific binding) and a considerably reduced matrix dependency (smaller signal differences to the system blank value in the case of analyte-free samples) which allows more precise tests.

EXAMPLE 5

Results in a CA 15-3 Test

The CA 15-3 test (Roche Diagnostics GmbH, Order No. 1776169) is a sandwich assay in a two-step test format. In the first step beads, sample, and the biotinylated antibody are incubated, subsequently the beads are magnetically separated, and the supernatant is aspirated. After several washing steps (adding washing buffer, aspirating again, resuspending by vortexing in washing buffer, separating again, aspiration) the beads were resuspended in reagent 2 of the CA 15-3 test from Roche which contains the ruthenylated antibody. After a further incubation they were washed again, subsequently the beads resuspended in washing buffer were transferred to a measuring cell of an ELECSYS E1010 instrument, and the amount of ruthenium label bound to the analyte was determined.

In the CA 15-3 test, bead aggregation is a particular problem; the analyte is an antigen with multiple repetitive elements which enable the binding of several antibody-bead complexes. During the washing steps the beads are deposited on relatively small areas and thus come into close proximity. This can result in the formation of three-dimensional complexes. These clumps of larger aggregates are visible on the measuring cell and result in poor precision (higher coefficient of variation) and low signal yields.

The aggregates are easy to see in colour pictures but can be hardly discerned in black and white pictures in various grey tones which is why such a figure was omitted. The coated beads have a major effect on the extent of aggregate formation on the measuring electrode. In contrast to standard SA beads, beads coated according to the invention in some cases show a considerably improved distribution on the measuring cell due to considerably less aggregation. This is irrespective of whether M-270 epoxy beads or hydrophobic M-280 beads were used for the coating. In both cases there is a considerably more homogeneous distribution on the electrode compared to the reference.

An improved bead distribution also leads to an improved signal recovery. The corresponding results of a representative CA 15-3 test are summarized in Table 4.

TABLE 4

Signal levels when using different beads in a CA 15-3 test (mean of a 12-fold determination)

| | | beads | |
|---|---|---|---|
| sample | reference | WJ069A beads (alkaline coated M-270 epoxide beads) | WJ069E beads (alkaline coated M-280 beads) |
| calibrator 1 29.9 µ/ml | 35,942 | 47,739 | 54,746 |
| calibrator 2 139 µ/ml | 237,460 | 304,448 | 354,975 |

This table shows that when using identical raw materials the use of different bead lots leads to different signal levels in the CA 15-3 test. The signal level is considerably improved in the case of the alkaline coated particles.

The coefficients of variation were determined using the CA 15-3 test from Roche Diagnostics GmbH (order No. 1776169) according to the manufacturer's instructions. Bead preparations listed in Table 5 were used instead of the coated beads from the test kit.

The coefficient of variation is determined by the conventional statistical method from a 21-fold determination of the sample.

TABLE 5

Coefficients of variations of various bead lots in the CA 15-3 test

| | lot | | | | |
|---|---|---|---|---|---|
| | standard coating | | | alkaline determination | |
| sample | A188 | A191 | 1:1 of A188/191 | R82 | WJ0075D |
| serum | 4.8 | 7.4 | 6.0 | 6.1 | 4.0 |
| CA 15-3 standard | 5.5 | 6.3 | 6.2 | 4.5 | 3.2 |

Table 5 shown above shows as an example that particles that have been loaded under the alkaline coating conditions according to the invention have considerably lower coefficients of variation (CV—expressed in percent of measured counts) in the CA 15-3 test. The lower the CV, the more precise is the determination of the analyte molecule.

LIST OF REFERENCES

DE 19924643
U.S. Pat. No. 4,478,914
U.S. Pat. No. 4,656,252
WO 96/03652
Lagaly, G., et al. Photonenkorrelationsspektroskopie in "Dispersionen und Emulsionen" (1997) 289-294, Darmstadt, Steinkopf
Conradie, J. D., et al., J. Immunol. Methods 59 (1983) 289-299
Ishikawa, E., et al., J. Immunoassay 1 (1980) 385-398

What is claimed is:

1. A method for producing protein-coated polystyrene microparticles consisting of the steps of:
   (a) combining a suspension of uncoated polystyrene microparticles with a protein to form a combination, the protein being a partner of a bioaffinity binding pair and having a size from 10 nm to 300 nm as determined by photon correlation spectroscopy,
   (b) coating the protein onto the microparticles by adsorption, wherein said coating step is conducted for a period of 1 to 10 days at a pH selected from a range of 10.5 to 12.5, and
   (c) separating the non-adsorbed protein from the protein-coated microparticles.

2. The method of claim 1, wherein the protein is a polymerized protein.

3. The method of claim 1, wherein the protein is a streptavidin which has been polymerized by chemical treatment.

4. The method of claim 1, wherein the microparticles have a magnetizable core.

5. The method of claim 4 wherein the microparticles have a size of 2.8 um and consist of 88% polystyrene and 12% magnetite.

6. The method of claim 1 wherein said coating step is conducted for a period of 4 to 7 days.

7. The method of claim 1 wherein the coating step is conducted at a pH between 11 and 12.

8. A method of producing protein-coated polystyrene microparticles, said method consisting of the steps of:

(a) combining a suspension of polystyrene microparticles with a protein to form a combination, the protein being a partner of a bioaffinity binding pair and having a size from 10 nm to 300 nm as determined by photon correlation spectroscopy,
(b) coating the protein onto the polystyrene microparticles by adsorption, wherein said coating step is conducted using a buffer having a salt content of 0.3 to 1.5 M and a pH selected from a range between 10.5 and 12.5, for a period of 1 to 10 days, and
(c) separating the non-adsorbed protein from the protein-coated microparticles.

* * * * *